US012741051B2

(12) United States Patent
Kim et al.

(10) Patent No.: US 12,741,051 B2
(45) Date of Patent: Sep. 22, 2026

(54) MEDICAL COMPOSITION COMPRISING ADIPOSE TISSUE-DERIVED EXTRACELLULAR MATRIX AND METHOD FOR PREPARING SAME

(71) Applicant: L&C Bio Co., Ltd., Gyeonggi-do (KR)

(72) Inventors: Sang Chul Kim, Seoul (KR); Kee Won Lee, Seoul (KR); Hyung Gu Kim, Seoul (KR); Whan Chul Lee, Seoul (KR)

(73) Assignee: L&C BIO CO., LTD., Gyeonggi-do (KR)

( * ) Notice: Subject to any disclaimer, the term of this patent is extended or adjusted under 35 U.S.C. 154(b) by 1040 days.

(21) Appl. No.: 17/781,862

(22) PCT Filed: Dec. 17, 2019

(86) PCT No.: PCT/KR2019/017878
§ 371 (c)(1),
(2) Date: Jun. 2, 2022

(87) PCT Pub. No.: WO2021/125373
PCT Pub. Date: Jun. 24, 2021

(65) Prior Publication Data

US 2023/0044236 A1 Feb. 9, 2023

(51) Int. Cl.
*A61L 15/22* (2006.01)
*A61L 15/28* (2006.01)
(Continued)

(52) U.S. Cl.
CPC ............. *A61L 15/225* (2013.01); *A61L 15/28* (2013.01); *A61L 15/34* (2013.01); *A61L 15/40* (2013.01); *A61L 27/20* (2013.01)

(58) Field of Classification Search
CPC .................................................... A61L 15/225
See application file for complete search history.

(56) References Cited

U.S. PATENT DOCUMENTS 10,456,347 B2 10/2019 Kim et al.
10,549,010 B2 2/2020 Lee et al.
(Continued)

FOREIGN PATENT DOCUMENTS

KR 20100136811 A 12/2010
KR 20130118418 A 10/2013
(Continued)

OTHER PUBLICATIONS

Flynn, L.E., "The use of decellularized adipose tissue to provide an inductive microenvironment for the adipogenic differentiation of human adipose-derived stem cells", Biomaterials, Jun. 2010; 31(17): 4715-24.

(Continued)

*Primary Examiner* — Sarah Alawadi
(74) *Attorney, Agent, or Firm* — McNeill PLLC

(57) ABSTRACT

The present invention relates to a medical composition and a method for preparing the same, the medical composition comprising: an adipose tissue-derived extracellular matrix powder; and a biocompatible polymer or a crosslinked product of the biocompatible polymer. The medical composition according to the present invention exists in a well-aggregated state even after implantation in the body and can maintain the volume thereof for a certain time.

4 Claims, 5 Drawing Sheets

(51) Int. Cl.

| | |
|---|---|
| ***A61L 15/34*** | (2006.01) |
| ***A61L 15/40*** | (2006.01) |
| ***A61L 27/20*** | (2006.01) |

(56) References Cited

U.S. PATENT DOCUMENTS

| | | | |
|---|---|---|---|
| 10,821,205 B2 * | 11/2020 | Xu | A61L 27/3683 |
| 11,078,461 B2 * | 8/2021 | Nahas | A61K 35/35 |
| 2012/0264190 A1 | 10/2012 | Christman et al. | |
| 2017/0119826 A1 | 5/2017 | Huang et al. | |

FOREIGN PATENT DOCUMENTS

| | | | |
|---|---|---|---|
| KR | 20150128481 A | | 11/2015 |
| KR | 20150143311 A | | 12/2015 |
| KR | 101628821 B1 | | 6/2016 |
| KR | 2019-0084840 | * | 7/2019 |
| WO | WO2016074794 | * | 5/2016 |
| WO | 2019079570 A1 | | 4/2019 |

OTHER PUBLICATIONS

Giatsidis, Giorgio, et al., "Preclinical Optimization of a Shelf-Ready, Injectable, Human-Derived, Decellularized Allograft Adipose Matrix", Tissue Eng Part A. Feb. 2019; 25 (3-4): 271-287.

International Search Report and Written Opinion of PCT/KR2019/017878, mailed Sep. 17, 2020, 10 pages.

Sengyoku, Hideyori et al., "Sodium hydroxide based non-detergent decellularizing solution for rat lung", Organogenesis, 14:94-106, 2018.

Wang, Lina, et al. "Combining decellularized human adipose tissue extracellular matrix and adipose-derived stem calls for adipose tissue engineering", Acta Biomater. Nov. 2013; 9(11): 8921-31.

Zhao, Yu et al., "Biocompatibility of injectable hydrogel from decellularized human adipose tissue in vitro and in vivo", Journal of Biomedical Materials Research Part B: Applied Biomaterials, vol. 107, Issue 5, p. 1684-1694, Oct. 23, 2018.

* cited by examiner

[FIG. 1]
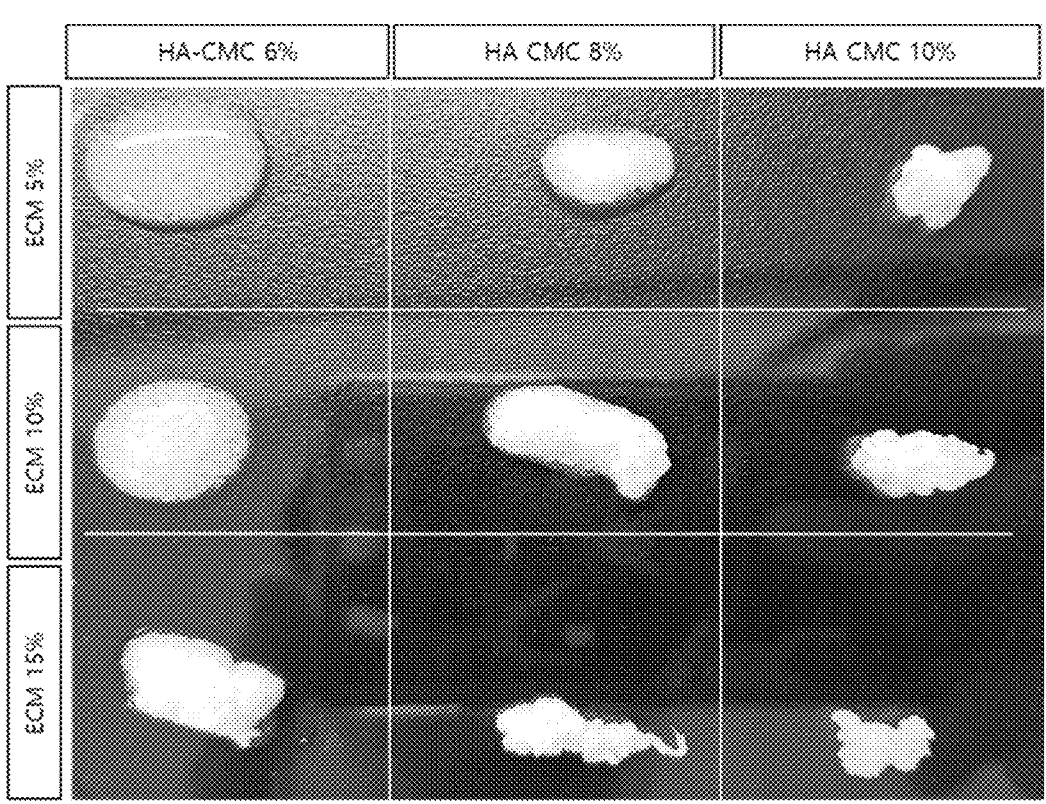

[FIG. 2]
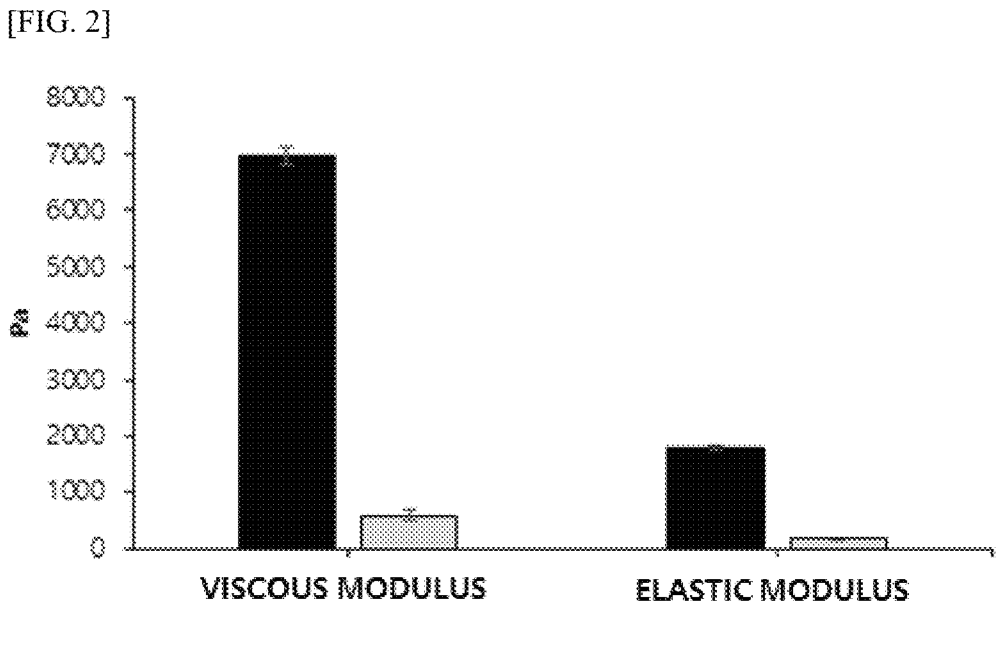
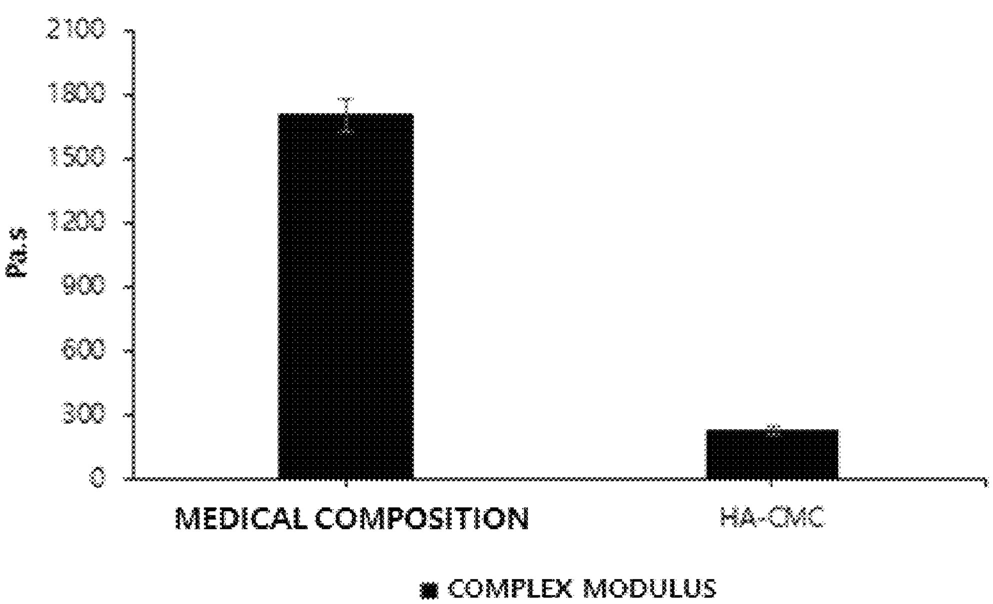

[FIG. 3]
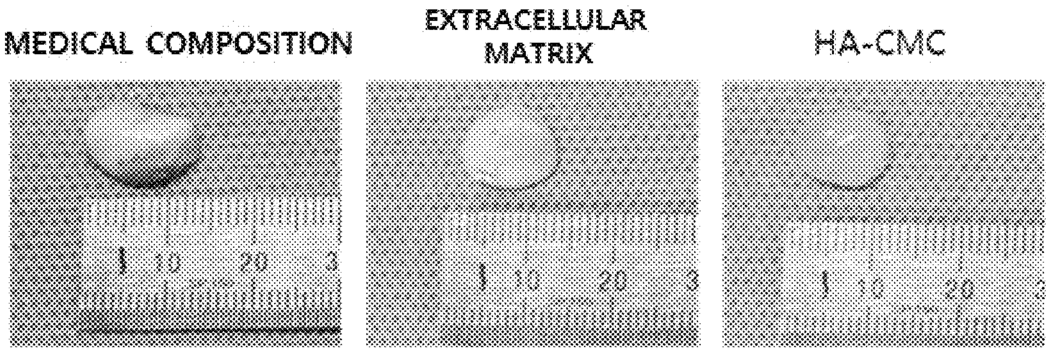
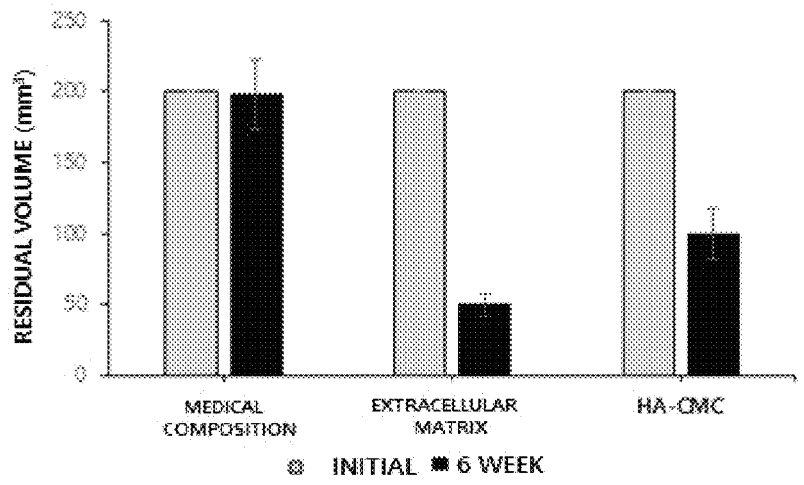

[FIG. 4]
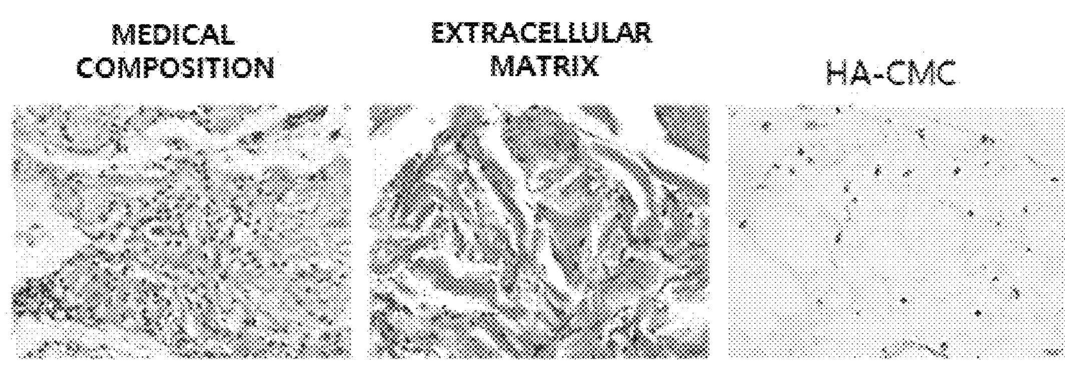
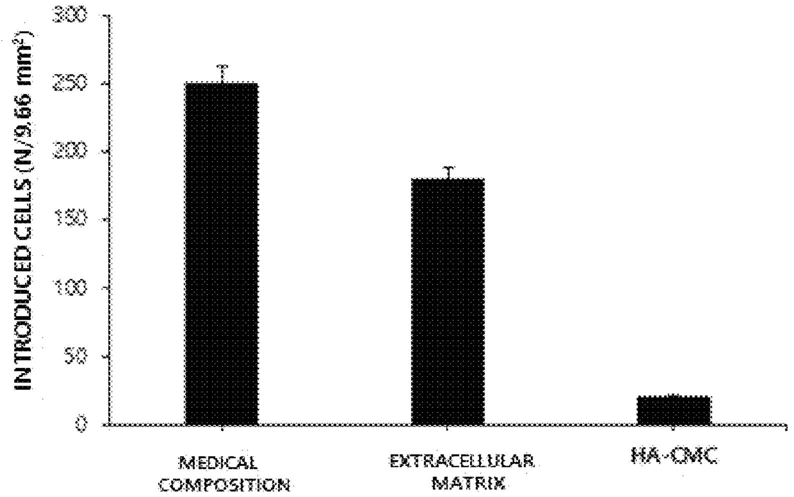

[FIG. 5]
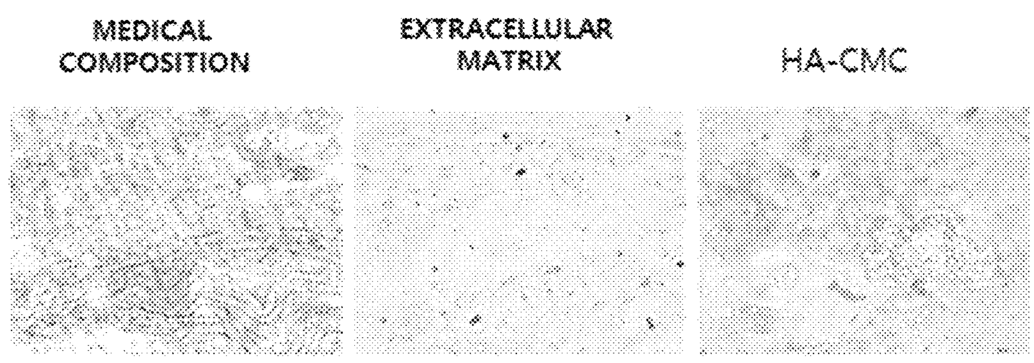
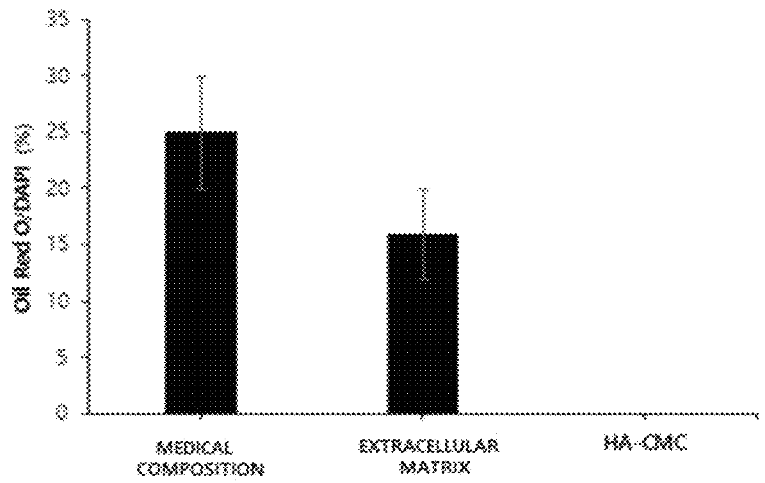

MEDICAL COMPOSITION COMPRISING ADIPOSE TISSUE-DERIVED EXTRACELLULAR MATRIX AND METHOD FOR PREPARING SAME

CROSS-REFERENCE TO RELATED APPLICATIONS

This application is a national phase entry pursuant to 35 U.S.C. § 371 of International Application No. PCT/KR2019/017878, filed Dec. 17, 2019, which is incorporated by reference herein in its entirety for any purpose.

TECHNICAL FIELD

The present invention relates to a medical composition comprising an adipose tissue-derived extracellular matrix and a method of preparing the same. More particularly, the present invention relates to a medical composition, which comprises an allogeneic or heterologous adipose tissue-derived extracellular matrix powder; a biocompatible polymer or a crosslinked product of a biocompatible polymer, and a method of preparing the same.

TECHNICAL FIELD

Regenerative medicine aims to replace or regenerate human cells, tissue, and organs. Physical trauma that causes tissue damage and functional loss and the emergence of new diseases caused by the advancement of society provide the inevitable motivation for more rapid development of the field of regenerative medicine.

Medical materials used in the field of regenerative medicine have to be deliberately selected according to the type of tissue or organ to be applied to, the type of disease or trauma, and a patient's medical history. Typically, materials most frequently selected for research are heterologous collagen and gelatin, microorganism-derived hyaluronic acid, chitosan, a vegetable cellulose-based polymer, and vegetable alginate. In addition, allogeneic materials that can be obtained from human corpses are also attracting attention as effective biomaterials that can be safely used in the field of regenerative medicine.

Safety, effectiveness, and economic/industrial interests of, particularly, adipose tissue among biomaterials are growing at home and abroad. Adipose tissue is a loose connective tissue composed of adipocytes, preadipocytes, fibroblasts, vascular endothelial cells, and various immune cells. Adipose tissue contains an extracellular matrix such as collagen, elastin, laminin, fibronectin, or glycosaminoglycan. An extracellular matrix not only helps the support and proliferation of cells in tissue in the body but also maintains the composition of tissue by binding with cells, resulting in helping in the recovery of a damaged area of the body.

In one example, it was reported that the human adipose tissue-derived extracellular matrix product, Renuva® (MTF Biologics), is effective in tissue repair when applied to a defective area such as a foot ulcer. As another example, it was reported that the human adipose tissue-derived extracellular matrix product, Allofill® (Biologica Technologies), is effective in wrinkle improvement. However, a medical product such as Renuva® or Allofill® has a disadvantage in that it is difficult to maintain the volume in the body after use because the microparticulated human adipose tissue-derived extracellular matrix powder is provided in a simple form hydrated in sterile physiological saline.

Patent Documents

1. Korean Patent No. 10-0771058
2. Korean Patent No. 10-1628821

Non-Patent Documents

1. Combining decellularized human adipose tissue extracellular matrix and adipose-derived stem cells for adipose tissue engineering, Acta Biomaterialia 2013, 8921-31
2. Biocompatibility of injectable hydrogel from decellularized human adipose tissue in vitro and in vivo, Journal of Biomedical Materials Research Part B, 2018, 1684-1694
3. The use of decellularized adipose tissue to provide an inductive microenvironment for the adipogenic differentiation of human adipose-derived stem cells, Biomaterials, 2010, 4715-24
4. Preclinical Optimization of a Shelf-Ready, Injectable, Human-Derived, Decellularized Allograft Adipose Matrix, Tissue Engineering Part A 2019, Vol. 25, No. 3-4

DISCLOSURE

Technical Problem

Therefore, the present invention is directed to providing a medical composition that is well agglomerated after being transplanted into the body, able to maintain its volume for a predetermined time, and a method of preparing the same.

More particularly, the present invention is directed to providing a medical composition that can promote the production of autologous fat and induce autologous reconstruction after transplantation into the body, and have excellent volume retention in the body due to an improved viscoelastic property by using an allogeneic or heterologous adipose tissue-derived extracellular matrix powder and a chemically-crosslinked biocompatible polymer, and a method of preparing the same.

Technical Solution

The present invention provides a medical composition that comprises an adipose tissue-derived extracellular matrix powder; and a biocompatible polymer or a crosslinked product of a biocompatible polymer.

The present invention also provides a method of preparing a medical composition, which comprises mixing an adipose tissue-derived extracellular matrix powder with a biocompatible polymer or a crosslinked product of a biocompatible polymer.

Advantageous Effects

The present invention provides a medical composition that comprises an adipose tissue-derived extracellular matrix powder; a biocompatible polymer or a crosslinked product of a biocompatible polymer, and a method of preparing the same.

The medical composition according to the present invention can be well agglomerated after being transplanted into the body, and maintain its volume for a predetermined time. Particularly, the composition of the present invention uses an allogeneic or heterologous adipose tissue-derived extracellular matrix powder and a chemically-crosslinked biocompatible polymer to promote the production of autologous fat and induce autologous reconstruction after transplantation into the body which and have excellent volume retention in the body due to improved viscoelastic property.

DESCRIPTION OF DRAWINGS

FIG. 1 is a set of images for showing physical properties according to a mixing ratio of an extracellular matrix powder and a crosslinked product of a biocompatible polymer during gamma sterilization in the preparation of a medical composition according to an embodiment of the present invention.

FIG. 2 is a set of graphs showing the viscous modulus, elastic modulus, and complex viscosity of a medical composition according to an embodiment of the present invention.

FIG. 3 shows an image of a composition extracted from a nude mouse 6 weeks after the injection of a medical composition according to an embodiment of the present invention and a graph showing the volume of the composition.

FIG. 4 shows a hematoxylin and eosin (H&E)-stained image for histologically analyzing a composition extracted from a nude mouse 6 weeks after the injection of a medical composition according to an embodiment of the present invention, and a graph showing the quantification of cell influx.

FIG. 5 shows an Oil Red O-stained image for analyzing fat production in a composition extracted from a nude mouse 6 weeks after the injection of a medical composition according to an embodiment of the present invention, and a graph showing the quantification of fat production.

MODES OF THE INVENTION

The present invention relates to a medical composition that comprises an adipose tissue-derived extracellular matrix powder; and a biocompatible polymer or a crosslinked product of a biocompatible polymer.

According to one embodiment of the present invention, a medical composition comprising an adipose tissue-derived extracellular matrix powder; and a biocompatible polymer or a crosslinked product of a biocompatible polymer was prepared, and it was confirmed that the medical composition may maintain a dosage form even after sterilization by irradiation, and have an excellent viscoelastic property. In addition, as a result of carrying out an in vivo experiment on the medical composition, it was confirmed that the composition has excellent volume retention ability in the body, autologous reconstruction, and autologous fat production compared to when using HA-CMC carriers.

Hereinafter, the medical composition according to the present invention will be described in further detail.

The medical composition of the present invention comprises an adipose tissue-derived extracellular matrix powder; and a biocompatible polymer or a crosslinked product of a biocompatible polymer.

In the present invention, the adipose tissue-derived extracellular matrix powder (hereinafter, referred to as an extracellular matrix powder) may be used as a medical material to promote autologous fat production and induce autologous reconstruction after transplantation into the body.

In one embodiment, the extracellular matrix (ECM) refers to a complex assembly of biopolymers filling the space in tissue or outside a cell. The extracellular matrix may have different components according to the type of cell or the degree of cell differentiation, and consist of a fibrous protein such as collagen or elastin, a complex protein such as proteoglycan or glycosaminoglycan, and a cell-adhesion glycoprotein such as fibronectin or laminin.

In one embodiment, the adipose tissue may be an allogeneic or heterologous adipose tissue. The "allogeneic" means human-derived, and the "heterologous" means being derived from animals other than a human, that is, mammals such as a pig, a cow or a horse, and fish.

In one embodiment, the adipose tissue-derived extracellular matrix powder has an average particle diameter of 100 to 800 μm. Within the particle diameter range, the powder is suitable for in vivo injection and can be injected with a syringe.

In one embodiment, the content of the adipose tissue-derived extracellular matrix powder may be 1 to 30, 5 to 15, or 3 to 8 parts by weight concerning the total weight of the composition. Within this range, the powder can be injected with a syringe.

In the present invention, the biocompatible polymer or crosslinked product of a biocompatible polymer may improve the viscoelastic property of the medical composition, and volume retention ability in the body. Here, the crosslinked product of a biocompatible polymer means one or more types of biocompatible polymers that are chemically crosslinked.

In one embodiment, the molecular weight of the biocompatible polymer or the crosslinked product of a biocompatible polymer may be 10 kDa to 2 MDa.

In one embodiment, as the biocompatible polymer, one or more selected from the group consisting of collagen, hyaluronic acid, chitosan, carboxymethylcellulose, alginate, and gelatin may be used.

In one embodiment, the crosslinked product of a biocompatible polymer may be a crosslinked product of one or more biocompatible polymers selected from the group consisting of collagen, hyaluronic acid, chitosan, carboxymethylcellulose, alginate, and gelatin.

In one embodiment, the biocompatible polymer may be crosslinked by a crosslinking agent, and the crosslinking agent may be one or more selected from the group consisting of 1,4-butanediol diglycidyl ether (BDDE), ethylene glycol diglycidyl ether (EGDGE), 1,6-hexanediol diglycidyl ether, propylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, tri-methylpropane polyglycidyl ether, 1,2-(bis(2,3-epoxypropoxy)ethylene, pentaerythritol polyglycidyl ether, and sorbitol polyglycidyl ether.

In one embodiment, the content of the biocompatible polymer may be 0.1 to 20, 1 to 15, 1 to 11, or 9 to 11 parts by weight concerning the total weight of the composition. Within this range, the physical properties of the biocompatible polymer may be improved, and the volume retention ability in the body may also be improved.

In the present invention, the medical composition may have a viscous modulus of 3,000 to 20,000 Pa, an elastic modulus of 1,000 to 10,000 Pa, and complex viscosity of 1,000 to 10,000 Pa·s. The viscous modulus, elastic modulus, and the complex viscosity refer to values measured by a rotary rheometer analyzer (frequency: 0.1 to 10 Hz, temperature: 25° C., strain: 1%).

"Viscoelasticity" refers to a phenomenon in which the properties of a liquid and the properties of a solid appear at the same time when a force is applied to an object. In the present invention, the viscous modulus, the elastic modulus, and the complex viscosity may be measured by measuring a resistance force and a dissipating force concerning a force applied to the composition.

The "viscous modulus (loss modulus, G')" is a measure of lost energy, indicating the viscous component of material. In the present invention, the viscous modulus of the medical composition may be 5,000 to 10,000 or 6,000 to 8,000 Pa. The "elastic modulus (storage modulus, G')" refers to the ratio of stress and strain that an elastic body has within the elastic limit. As the elastic modulus increases, the composition becomes harder and has a higher ability to resist deformation. In the present invention, the elastic modulus of the medical composition may be 1,000 to 5,000 Pa or 1,000 to 3,000 Pa. The "complex viscosity" is a frequency-dependent viscosity calculated by a vibration measurement method, and is a value reflecting G", G' and the frequency value measured. In the present invention, the complex viscosity of the medical composition may be 1,000 to 3,000 Pa·s or 1,500 to 2,500 Pa·s.

In addition, the extrusion force, that is, the injection pressure of the medical composition may be 110 N or less. In the present invention, the extrusion force is a value measured using a universal material tester, and specifically, is the maximum load value (N) obtained when the contents in a syringe (20 G) are discharged out of a cannula by fastening the cannula to the syringe (20 G) and pressing the syringe at a test speed of 12 mm/min.

The "extrusion force" refers to an extrusion force at an injection rate that is comfortable for a patient. The rate that is "comfortable for a patient" is used to define an injection speed that does not cause an injury or excessive pain to a patient when injected into the skin. The "comfort" used herein includes not only comfort or ability to inject a composition by a doctor or medical professional but patient comfort. Generally, having a low extrusion force does not cause tenderness upon injection of the composition and is easy to control. In the present invention, the extrusion force of the medical composition may be 100 N or less, 70 N or less, 60 N or less, 40 N or less, 35 N or less, or 30 N or less.

In one embodiment, the medical composition of the present invention may be injected or inserted into the body through injection with a syringe. This medical composition may be used as a general medical material and used as a tissue repair agent, a filler, an anti-adhesion agent, a plastic surgery aid, an arthritis therapeutic agent, a wound dressing, a hemostatic agent, or a lipodystrophy therapeutic agent. Here, lipodystrophy has a symptom of the loss of adipose tissue, and the production of autologous fat may be promoted by the medical composition of the present invention.

In addition, the present invention relates to a method of preparing the above-described medical composition.

The method of preparing a medical composition may comprise mixing an adipose tissue-derived extracellular matrix powder with a biocompatible polymer or a cross-linked product of a biocompatible polymer.

In the present invention, as the adipose tissue-derived extracellular matrix powder, a commercially available product may be used, or the powder may be prepared in a laboratory and used.

The adipose tissue-derived extracellular matrix powder may be prepared by a delipidation step of removing a lipid component from adipose tissue;

a decellularization step of removing cells from the lipid component-removed adipose tissue;

a lyophilization step of lyophilizing the cell-removed adipose tissue; and a powderization step of powdering the lyophilized product.

In the present invention, a washing step may be performed before the delipidation step. In the washing step, the adipose tissue may be washed with sterile distilled water. Through this step, impurities in the adipose tissue may be removed.

In the present invention, the delipidation step is a step of removing a lipid component from adipose tissue.

In one embodiment, delipidation means the removal of a lipid component from tissue.

In one embodiment, the removal of a lipid component may be performed by physical treatment or chemical treatment, or a combination of the physical and chemical treatments. When the physical and chemical treatments are performed in combination, the order of performance is not limited.

In one embodiment, the type of physical treatment is not particularly limited, and the physical treatment may be performed through pulverization. The pulverization may be performed using a pulverizing means that is known in the art, such as a mixer, a homogenizer, a freezing grinder, an ultrasonic grinder, a hand blender, or a plunger mill.

In pulverization, the particle diameter of the pulverized product, that is, pulverized adipose tissue may be 0.01 to 1 mm.

In one embodiment, the type of chemical treatment is not particularly limited, and the chemical treatment may be performed using a delipidation solution. The delipidation solution may include a polar solvent, a non-polar solvent, or a mixed solvent thereof. The polar solvent may be water, alcohol, or a mixed solvent thereof, and the alcohol, methanol, ethanol or isopropyl alcohol may be used. The non-polar solvent may be heptane, octane, or a mixed solution thereof. Specifically, in the present invention, as a delipidation solution, a mixed solution of isopropyl alcohol and hexane may be used. Here, a mixing ratio of isopropyl alcohol and hexane may be 40:60 to 60:40.

The treatment time of the delipidation solution may be 4 to 30 hours or 10 to 20 hours.

In one embodiment, the delipidation step may be performed by sequentially applying physical treatment and chemical treatment. The lipid component may be first eliminated from the adipose tissue through physical treatment, and the lipid component that is not eliminated by the physical treatment may be removed by chemical treatment.

In the present invention, the decellularization step may be a step of removing cells from the adipose tissue from which the lipid component is removed in the delipidation step.

In one embodiment, decellularization means the removal of other cell components excluding the extracellular matrix from the tissue, for example, the nucleus, the cell membrane, nucleic acids, and the like.

In one embodiment, the decellularization may be performed using a basic solution, and as the basic solution, one or more selected from the group consisting of sodium hydroxide, potassium hydroxide, ammonium hydroxide, calcium carbonate, magnesium hydroxide, calcium hydroxide, and ammonia may be used. In the present invention, as the basic solution, sodium hydroxide (NaOH) may be used. In the present invention, since the basic solution is used in the decellularization step, there is an advantage of having no cytotoxicity.

In one embodiment, the concentration of the basic solution may be 0.01 to 1 N, 0.06 to 0.45 N, 0.06 to 0.2 N, or 0.08 to 1.02 N. Within this concentration range, it is easy to remove cells.

In addition, in one embodiment, the decellularization step may be performed for 60 to 48 minutes, 70 to 200 minutes, or 90 to 150 minutes. Within this time range, it is easy to remove cells.

In the present invention, after the decellularization step and before the lyophilization step, a centrifugation step may be additionally performed. Through the centrifugation step, impurities generated in the delipidation and decellularization steps may be removed and a high purity extracellular matrix material (precipitate) may be obtained.

In one embodiment, the centrifugation may be performed at 4,000 to 10,000 rpm, or 8,000 rpm for 5 to 30 minutes, 5 to 20 minutes, or 10 minutes.

In addition, before and/or after centrifugation, a washing step may be additionally performed, and for washing, sterile distilled water may be used.

In the present invention, the lyophilization step is a step of lyophilizing the product obtained after the above-described step, that is, the decellularization or centrifugation step. The lyophilization is a method of rapidly cooling the tissue that is in a frozen state and absorbing moisture under a vacuum, and through the lyophilization, the moisture in the extracellular matrix material may be adjusted, and powderization may be easily performed.

In one embodiment, the lyophilization may be performed at −50 to −80° C. for 24 to 96 hours.

In the present invention, the powderization step is a step of powdering the lyophilized product, that is, the extracellular matrix.

The particle diameter of the powdered extracellular matrix powder may be 100 to 800 μm.

In addition, the adipose tissue-derived extracellular matrix powder of the present invention may be prepared by a washing step of washing adipose tissue;

- a delipidation step of removing a lipid component from the washed adipose tissue;
- a decellularization step of removing cells from the lipid component-removed adipose tissue;
- a centrifugation step of centrifuging the decellularized adipose tissue;
- a lyophilization step of lyophilizing a precipitate obtained by the centrifugation; and
- a powderization step of powdering the lyophilized product.

In the present invention, a commercially available product may be used as the biocompatible polymer or the crosslinked product of a biocompatible polymer. In addition, the crosslinked product may be prepared using a biocompatible polymer in a laboratory and used.

The crosslinked product of a biocompatible polymer may be prepared by a crosslinking step of crosslinking a biocompatible polymer using a crosslinking agent; and

- a lyophilization step of lyophilizing the crosslinked product.

In the present invention, the crosslinking step is a step of crosslinking a biocompatible polymer using a crosslinking agent. In this step, the types of a biocompatible polymer and the crosslinking agent may be the same as described above.

In one embodiment, the biocompatible polymers may be bound through an amide bond.

In one embodiment, the content of the crosslinking agent may be 0.5 to 10 parts by weight concerning the biocompatible polymer.

In the present invention, the lyophilization step is a step of lyophilizing the crosslinked biocompatible polymer.

In one embodiment, the lyophilization may be performed at −50 to −80° C. for 24 to 96 hours.

In the present invention, the adipose tissue-derived extracellular matrix powder and the biocompatible polymer or the crosslinked product of a biocompatible polymer may be mixed by physical mixing.

In one embodiment, the content of the adipose tissue-derived extracellular matrix powder in the mixture may be 1 to 30 parts by weight, 5 to 15 parts by weight, or 3 to 8 parts by weight.

In addition, the content of the crosslinked product of a biocompatible polymer in the mixture may be 0.1 to 20 parts by weight, 1 to 15 parts by weight, 1 to 11 parts by weight, or 9 to 11 parts by weight.

In one embodiment, the mixture may be prepared by dissolving the lyophilized crosslinked product of a biocompatible polymer in a solvent and mixing it with the extracellular matrix powder. Here, as a solvent, physiological saline may be used.

The present invention may further comprise a step of sterilizing the mixture.

Through the sterilization step, the immunity of the medical composition may be eliminated, and bacteria may be effectively destroyed.

In one embodiment, the sterilization step may be performed by irradiation, and the irradiation range may be 10 to 30 kGy.

In addition, the present invention relates to the use of the above-described medical composition.

The medical composition according to the present invention may promote the production of autologous fat and induce autologous reconstruction after transplantation into the body, and have an improved viscoelastic property and thus exhibit excellent volume retention in the body.

Therefore, in one embodiment, the medical composition of the present invention may be injected or inserted into the body through injection with a syringe and used as a tissue repair agent, a filler, an anti-adhesion agent, a plastic surgery aid, an arthritis therapeutic agent, a wound dressing, a hemostatic agent, or a lipodystrophy therapeutic agent.

The present invention will be described in further detail concerning the following examples. However, the scope of the present invention is not limited to the following examples, and it will be understood by those of ordinary skill in the art that various modifications, alterations, or applications are possible without departing from the technical details derived from the details described in the accompanying claims.

EXAMPLES

Example 1. Medical Composition in which Human Adipose Tissue-Derived Extracellular Matrix Particles and Chemically-Crosslinked Biocompatible Polymer are Physically Mixed (1) Preparation of Human Adipose Tissue-Derived Extracellular Matrix Fat was eliminated by pulverizing human adipose tissue using a grinder. To remove the fat that was not eliminated, delipidation was carried out using 40% to 60% isopropyl alcohol and 40% to 60% hexane for 16 hours. Cells were removed by treating the fat-removed tissue with 0.1N sodium hydroxide (NaOH).

To wash the fat- and cell-removed extracellular matrix, supernatant was removed by centrifugation at 8,000 rpm for 10 minutes, and the washing procedure was repeated 5 to 10 times. The scaffold was lyophilized such that the water content in the human adipose tissue-derived extracellular matrix was 10% or less, and preferably 1% to 8%.

The lyophilized human adipose tissue-derived extracellular matrix was pulverized into microparticles using a micro grinder.

(2) Preparation of Chemically-Crosslinked Biocompatible Polymer

An HA-CMC carrier was prepared by mixing hyaluronic acid (HA) and carboxymethylcellulose (CMC) with 1,4-butanediol diglycidyl ether (BDDE).

Specifically, a reaction solvent was prepared by adding 1 to 10 mL of BDDE per 100 mL of an aqueous solution of 0.1 to 1 N sodium hydroxide. A mixed solution was prepared by adding 1 to 10 g of CMC and 1 to 20 g of HA to the reaction solvent and uniformly mixing them. The mixed solution was heated at 50° C. for 3 hours to perform crosslinking.

The crosslinked product was placed on a dialysis membrane to perform dialysis with 5 L of phosphate-buffered saline at room temperature. After two hours, the saline was replaced with 5 L of 50% EtOH, and dialysis was performed at room temperature for 1 hour. Afterward, dialysis was performed with sterile distilled water at room temperature for 72 hours, and the resulting product was lyophilized, thereby finally obtaining an HA-CMC carrier.

(3) Preparation of Medical Composition

The human adipose tissue-derived extracellular matrix (5 wt % to 15 wt %) prepared in (1) and the HA-CMC carrier (1 wt % to 10 wt %) prepared in (2) were mixed with sterile physiological saline.

The mixed final product was sterilized by 25 kGy gamma irradiation, thereby preparing a medical composition.

Experimental Example 1. Verification of Ability to Maintain Dosage Form During Sterilization of Medical Composition by Irradiation (1) Method The ability to maintain a dosage form of the medical composition prepared in Example 1 was verified.

Samples were prepared with the contents shown in Table 1 below (remainder: sterile physiological saline) and sterilized by 25 kGy gamma irradiation. In the gamma sterilization, physical properties according to the content ratio of each component were confirmed.

TABLE 1

| Sample No. | Content (%) of human adipose tissue-derived extracellular matrix | Carrier content (%) |
|---|---|---|
| 1 | 5 | 2 |
| 2 | 10 | 2 |
| 3 | 15 | 2 |
| 4 | 5 | 4 |
| 5 | 10 | 4 |
| 6 | 15 | 4 |
| 7 | 5 | 6 |
| 8 | 10 | 6 |
| 9 | 15 | 6 |
| 10 | 5 | 8 |
| 11 | 10 | 8 |
| 12 | 15 | 8 |
| 13 | 5 | 10 |
| 14 | 10 | 10 |
| 15 | 15 | 10 |

Meanwhile, an extrusion force was measured for each sample. The extrusion force was measured by fastening a cannula to a syringe containing contents using a universal material tester, and measuring the maximum load (N) when the contents in the syringe were discharged out of the cannula by pressing the syringe at a test speed of 12 mm/min.

(2) Results

The results of measurement of physical properties according to the content ratio of each component in gamma sterilization are shown in FIG. 1.

In addition, the result of the measurement of the extrusion force of each sample is shown in Table 2.

TABLE 2

| Sample No. | Content (%) of human extracellular matrix adipose tissue-derived | Carrier content (%) | Extrusion force (Injection pressure, N) 17G | 20G |
|---|---|---|---|---|
| 1 | 5 | 2 | 26N | 28N |
| 2 | 10 | 2 | 23N | 20N |
| 3 | 15 | 2 | 32N | 37N |
| 4 | 5 | 4 | 26N | 20N |
| 5 | 10 | 4 | 19N | 30N |
| 6 | 15 | 4 | 35N | 41N |
| 7 | 5 | 6 | 22N | 27N |
| 8 | 10 | 6 | 23N | 30N |
| 9 | 15 | 6 | 36N | 65N |
| 10 | 5 | 8 | 28N | 27N |
| 11 | 10 | 8 | 23N | 41N |
| 12 | 15 | 8 | 38N | 72N |
| 13 | 5 | 10 | 19N | 28N |
| 14 | 10 | 10 | 23N | 68N |
| 15 | 15 | 10 | 48N | 100N |

As shown in FIG. 1 and Table 2, it can be confirmed that a medical composition comprising 5 wt % of a human adipose tissue-derived extracellular matrix (ECM) and 10 wt % of an HA-CMC carrier has the best physical properties and an extrusion force of 40 N or less at 20 G, so that in vivo injection using a syringe is easy.

Experimental Example 2. Analysis of Viscoelastic Property of the Medical Composition (1) Method For comparison of viscoelastic properties, a medical composition comprising 5 wt % of the human adipose tissue-derived extracellular matrix (ECM) and 10 wt % of the HA-CMC carrier selected as the optimal mixing ratio in Experimental Example 1 (Sample 13) was used as an experimental group (medical composition), and a composition that did not comprise an extracellular matrix, but comprised 10 wt % HA-CMC was used as a control (HA-CMC).

Specifically, an elastic modulus, a viscous modulus, and a complex viscosity were measured with a rotary rheometer analyzer under conditions of a frequency of 0.1 to 10 Hz, a temperature of 25° C., and a strain of 1%.

(2) Results

The results of measuring an elastic modulus, a viscous modulus, and a complex viscosity are shown in FIG. 2.

As shown in FIG. 2, the medical composition according to the present invention showed approximately 7-fold higher elastic modulus and viscous modulus values, and a 6-fold higher complex viscosity value, compared to the control HA-CMC.

Experimental Example 3. Verification of In Vivo Performance of the Human Adipose Tissue-Derived Medical Composition (1) Method To verify the performance of a medical composition, an animal experiment was carried out.

The extracellular matrix powder (extracellular matrix) prepared in (1) of Example 1 and the HA-CMC carrier (HA-CMC) prepared in (2) of Example 1 were used as controls, and the medical composition comprising 5 wt % of the human adipose tissue-derived extracellular matrix (ECM) powder and 10 wt % of the HA-CMC carrier selected as the optimal mixing ratio in Experimental Example 1 (Sample 13) was used as an experimental group.

0.2 cc each of the compositions of the controls and the experimental group was transplanted into a BALB/c nude mouse via subcutaneous dorsal injection, and 6 weeks after injection, the experimental animals were sacrificed to analyze the results.

(2) Results (A) Verification of Volume Retention Ability in the Body

Six weeks after the injection of the compositions of the controls and experimental example, samples extracted from the nude mice were photographed, and volumes were measured using digital calipers.

FIG. 3 shows an image of the composition extracted from the nude mouse, and a graph showing the residual volume thereof.

As shown in FIG. 3, it can be confirmed that the medical composition as the experimental group shows excellent volume retention ability in the body, compared to HA-CMC and the extracellular matrix as the controls.

From the graph, it can be confirmed that, after 6 weeks, the volume retention of the medical composition is 4 times or more that of the extracellular matrix.

(B) Verification of Autologous Reconstruction

The samples extracted in (A) were used to confirm autologous reconstruction by histological staining. Hematoxylin and eosin (H&E) staining was performed for histological analysis, and cell influx was quantified.

FIG. 4 shows hematoxylin and eosin (H&E)-stained image for histologically analyzing a composition extracted from a nude mouse and a graph showing the quantification of cell influx.

As shown in FIG. 4, as a result of histological staining, cells were introduced into the medical composition as the experimental example, compared to HA-CMC and the extracellular matrix as the controls, and blood vessels were formed.

In addition, from the graph, it can be confirmed that, after six weeks, 8 times or more cells were introduced into the medical composition compared to HA-CMC.

(C) Verification of Autologous Fat Production Effect

Fat production from the samples extracted in (A) was verified.

To analyze the fat production in the extracted sample, Oil Red O staining was performed, and the fat production was quantified.

FIG. 5 shows an Oil Red O-stained image for analyzing fat production in a composition extracted from a nude mouse and a graph showing the quantification of fat production.

As shown in FIG. 5, as a result of the Oil Red O staining, it can be confirmed that the fat production in the medical composition as the experimental example is more induced than in HA-CMC and the extracellular matrix as the controls.

In addition, from the graph, after 6 weeks, it can be confirmed that fat production increased by 8% or more in the medical composition compared to the extracellular matrix.

INDUSTRIAL APPLICABILITY

A medical composition according to the present invention can promote autologous fat production and induce autologous reconstruction after transplantation into the body and has an excellent volume retention effect in the body due to improved viscoelastic property.

Therefore, the medical composition of the present invention can be injected or inserted into the body through injection using a syringe and can be used as a tissue repair agent, a filler, an anti-adhesion agent, a plastic surgery aid, an arthritis therapeutic agent, a wound dressing, a hemostatic agent, or a lipodystrophy therapeutic agent.

The invention claimed is:

1. A medical composition, comprising an adipose tissue-derived extracellular matrix powder and a crosslinked product of a biocompatible polymer, wherein the content of the adipose tissue-derived extracellular matrix powder is 3 to 8 parts by weight concerning the total weight of the composition, the content of the crosslinked product of a biocompatible polymer is 9 to 11 parts by weight concerning the total weight of the composition, and the crosslinked product of a biocompatible polymer is a crosslinked product of hyaluronic acid and carboxymethylcellulose, and the medical composition has a viscous modulus of 3,000 to 20,000 Pa, an elastic modulus of 1,000 to 10,000 Pa, a complex viscosity of 1,000 to 10,000 Pa·s, and an extrusion force of 110 N or less.

2. The composition of claim 1, wherein the adipose tissue-derived extracellular matrix powder has an average particle diameter of 100 to 800 μm.

3. The composition of claim 1, wherein the hyaluronic acid and carboxymethylcellulose are crosslinked by one or more crosslinking agents selected from the group consisting of 1,4-butanediol diglycidyl ether (BDDE), ethylene glycol diglycidyl ether (EGDGE), 1,6-hexanediol diglycidyl ether, propylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, tri-methylpropane polyglycidyl ether, 1,2-(bis(2,3-epoxypropoxy)ethylene, pentaerythritol polyglycidyl ether, and sorbitol polyglycidyl ether.

4. The composition of claim 1, wherein the medical composition is injectable.

* * * * *